United States Patent [19]

Nafarrate et al.

[11] Patent Number: 5,212,379
[45] Date of Patent: May 18, 1993

[54] FIBER OPTICAL MONITOR FOR DETECTING MOTION BASED ON CHANGES IN SPECKLE PATTERNS

[75] Inventors: Antonio B. Nafarrate, San Jose; Eric G. Rawson, Saratoga, both of Calif.

[73] Assignee: Alamed Corporation, Portola Valley, Calif.

[21] Appl. No.: 802,868

[22] Filed: Dec. 6, 1991

[51] Int. Cl.⁵ .............................................. H01J 40/14
[52] U.S. Cl. ........................ 250/227.14; 250/237.16
[58] Field of Search ................... 250/227.14, 227.16, 250/227.19, 227.11; 128/691, 666, 714

[56] References Cited

U.S. PATENT DOCUMENTS

| 4,297,684 | 10/1981 | Butter | 250/227.19 |
| 4,339,661 | 7/1982 | Pitt et al. | 250/227.19 |
| 4,843,233 | 6/1989 | Jeunhomme | 250/227.19 |

OTHER PUBLICATIONS

Eric G. Rawson and Joseph W. Goodman, Modal noise in multimode optical fibers, 1982, Society of Photo-Optical Instrumentation Engineers (SPIE) vol. 355, Fiber Optics: Short-Haul and Long-Haul Measurements and Applications, pp. 37–42.

Joseph W. Goodman and Eric G. Rawson, Statistics of Modal Noise in Fibers: a case of constrained speckle, Jul. 1981, Optics Letters, vol. 6, p. 324.

Primary Examiner—David C. Nelms
Assistant Examiner—Que T. Le
Attorney, Agent, or Firm—Oblon, Spivak, McClelland, Maier & Neustadt

[57] ABSTRACT

A motion monitor using coherent or partially coherent light passing through an optical fiber which is in contact or close to an object whose motion is to be monitored. An optical speckle pattern is formed near the output of the optical fiber which pattern changes as the fiber moves in response to the motion of the object being monitored. An optical detector monitors all or a part of the speckle pattern and electronically processes the optical detector's electrical output signals to derive information on the status of the object being monitored.

19 Claims, 2 Drawing Sheets

FIBER OPTICAL MONITOR FOR DETECTING MOTION BASED ON CHANGES IN SPECKLE PATTERNS

BACKGROUND OF THE INVENTION

A significant cause of death in infants (birth to about 2 years) is the "Crib Death" or Sudden Infant Death Syndrome (SIDS). Medical authorities in general agree that some infants simply stop breathing during sleep (apnea) and that death can be prevented if the condition is detected and help is provided within a short time (some 30 to 60 seconds) by trained personnel or parents (using mouth to mouth resuscitation or similar techniques).

Apnea monitors already exist but their cost (on the order of $ 1000) creates an affordability problem that limits their use. Furthermore, the existing monitors produce considerable numbers of false alarms in infants with shallow breathing.

SUMMARY OF THE INVENTION

We have invented a less expensive and inherently more reliable monitoring device based on detection of modal noise produced by minute motions in a single- or multimode-optical fiber illuminated by a coherent or partially coherent light source such as a laser. A few feet or meters of fiber are curved and woven into or attached to a blanket, mattress cover, or other convenient bedding materials, or clothing pieces of the individual being monitored. Coherent light from a gas laser or a laser diode is injected at the input end of the fiber. At least part (preferably about one half) of the laser light emerging from the output end of the fiber illuminates a photodiode (i.e., a photo detector). That is, the photodiode detects the optical power in either a near-field or far-field speckle pattern in an area corresponding optimally to approximately half of the speckle "cells," or speckle correlation areas. Alternatively, a polarizing filter is placed between the detector and the fiber's output end, which passes about half the guided light, namely, that light which is polarized in the direction which is transmitted by the polarizing filter. In this way the photo detector generates a fluctuating signal whose amplitude and frequency spectrum are related to mechanical motions of the fiber.

In practice, normal respiration motions will induce small bendings in the fiber, changing the speckle pattern and producing in the photodiode a corresponding "modal noise" signal. This signal may be a voltage signal or a current signal, depending on the type of detector used and the electronic circuit in which it is used. Without loss of generality, and for simplicity henceforth, we will refer simply to this signal as the "noise current." The highest frequency with which the detected noise current fluctuates will be proportional to the velocity of motion of the fiber. Thus, normal breathing will be characterized by a periodic substantial increase in the power of the higher frequency components of the detected noise current. Perturbed respiration, on the other hand, will produce a significantly different noise current spectrum versus time, as will of course cessation of breathing. This persistent abnormality in the frequency spectrum of the noise current can be used to electronically trigger a suitable alarm or alarms, summoning timely aid.

In addition to detecting apnea, it will be observed by those skilled in the art that this invention is also capable of detecting, and triggering an appropriate alarm response to, other breathing anomalies such as rapid or otherwise distressed breathing, as well as irregular heartbeat. Such other alarm(s) could conveniently be distinct from the apnea alarm. If multiple conditions and/or plural individuals are being monitored simultaneously, easily discernible alarms could be used to facilitate the identification of the reason and source for any alarm that is given.

Additionally, a device of the foregoing type can also be used to monitor certain normal bodily functions. Examples are the monitoring of normal respiration and heartbeat in a medical treadmill test, and around-the-clock monitoring of respiration and/or heartbeat by attaching the invention to an ambulatory recording device or a wireless transmitting device which transmits data from the individual that is being monitored to a remote recording device.

Furthermore, such a device can also be used to monitor the motions of animals other than humans or of non-animate objects, such as machines with moving mechanical parts.

The longer the sensor portion of the optical fiber that is used (that is, that portion comprising the middle section that is mechanically attached to the object or individual being monitored, and excluding the input and output ends), the greater will be the sensitivity of the output speckle pattern to movements of the object or individual being monitored. The longer the fiber, however, the greater will be its purchase and assembly costs and its optical attenuation of the laser light which propagates through it. Thus, the optimal length of optical fiber used in this invention will be governed by a balance of these factors. Lengths of the order of one to a few meters have been found to be suitable.

BRIEF DESCRIPTION OF THE DRAWINGS

A clear understanding of the present invention may be achieved by a perusal of the following detailed description of illustrated embodiments and the attached drawings in which.

DETAILED DESCRIPTION OF THE ILLUSTRATED EMBODIMENTS

Figure 1:
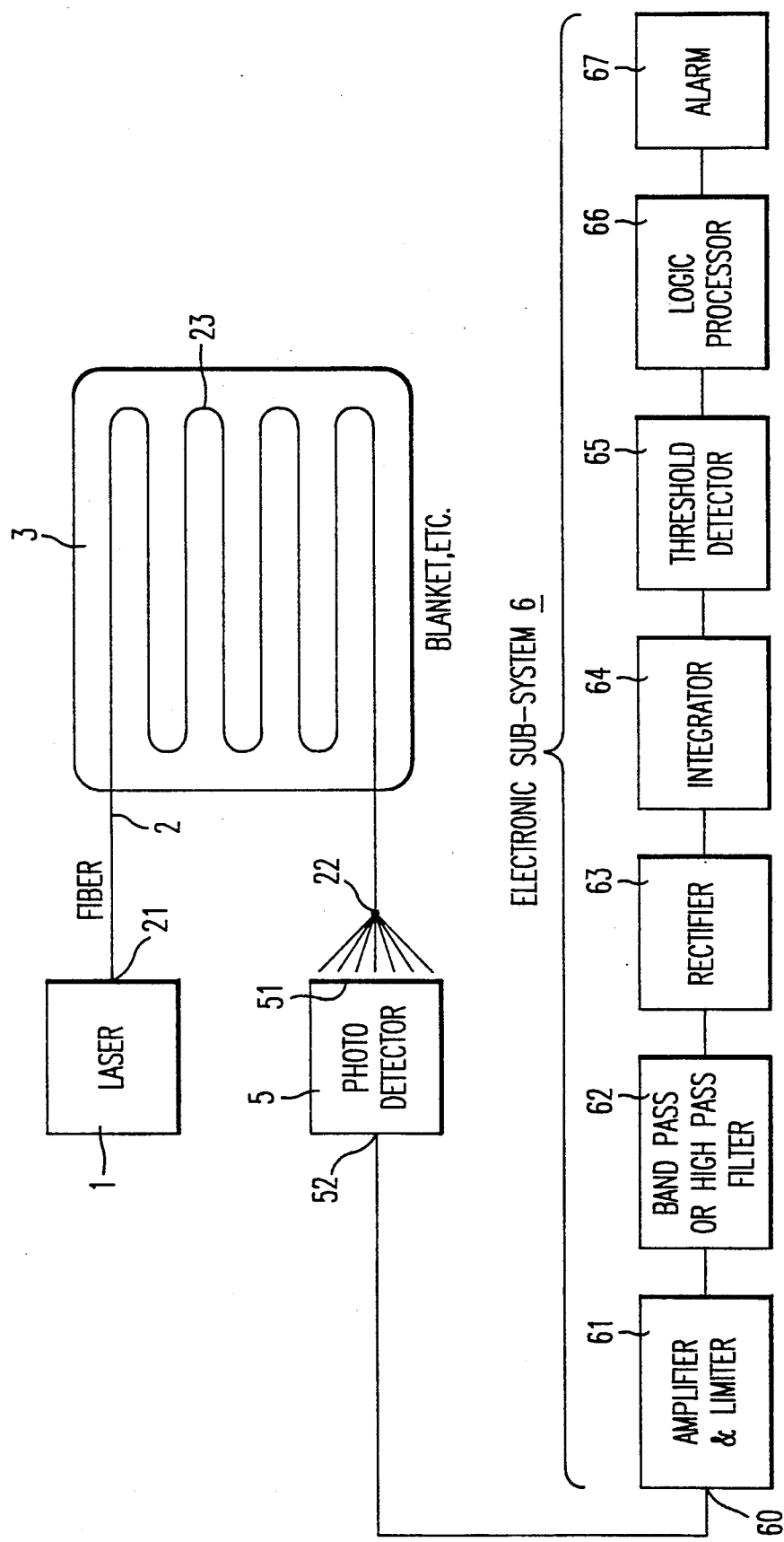
FIG. 1 is a simplified functional diagram of an apnea alarm and heartbeat monitor system according to the present invention.

Detection of a part, but not all, of the light emerging from the optical fiber is preferred because as determined by the inventors, for a given laser light source, fiber, and detector sensitivity, the noise current has a maximum value when the optical detector is illuminated by half the guided modes of the optical fiber. This condition is achieved in either of two ways: positioning the detector so it is exposed to half the speckle cells in the speckle pattern; or positioning the detector so it is illuminated by all speckle cells and interposing a polarizing filter between the detector and the output end of the fiber, which polarizing filter passes only one of the two orthogonal polarizations of the light emerging from the fiber. We henceforth refer to these two cases as the "spatial filter case" and the "polarizing filter case," respectively. In the spatial filter case, and for a step-index optical fiber, this means the detector preferably subtends approximately half the area of either the near field or the far field of the light emerging from the optical fiber. In the spatial filter case for a parabolic index fiber (also called a "gradient index" fiber), the speckle sizes vary across both the near- and far-field, so the optimal detection area is not in general equal to half the full field area; but the optimal area for the detector is still that which subtends half the speckle cells. It may be noted that in the scientific literature speckle cells are sometimes termed "speckle correlation areas."

It is to be understood, however, that this invention is not limited to the use of a detector that is illuminated by approximately half the speckle cells, as described above, nor is it necessary to use a polarizing filter to likewise limit by half the number of guided modes illuminating the detector. Detection of more or less than half of the output light from the fiber will still result in a functioning system, but one with a smaller average noise current. In particular, the detector can be illuminated by essentially all the light emerging from the optical fiber; however, the modal noise associated with this case will be significantly less than when approximately half of the emerging light is detected.

More particularly, the modal noise modulation mechanism can be understood as follows. Some light, which a moment before was guided in certain high-order guided modes (i.e., modes propagating at such large angles to the fiber axis that they are close to the radiative "cut-off" angle), may be switched into non-guided (radiative) modes (i.e., modes propagating at angles exceeding the cut-off angle) when the fiber moves, contributing to a reduction in the total guided optical power. Similarly, fiber motion may cause some light, which a moment before was being coupled into radiative modes (and thus being lost from the fiber), to be switched back into guided modes, contributing to an increase in the total guided optical power. Thus, modal noise current fluctuations are generated when the fiber moves, even in the case where the detector is illuminated by all the guided modes. While we note that the RMS amplitude of the noise current in the full-field detection case is less than that of the half-field detection case, the simplicity of full-field detection may make it a useful option despite this reduced sensitivity to motion.

As will be appreciated by one skilled in the art, the speckle pattern is essentially an optical interferometric effect. Thus, it is to be understood that optical interferometric measurement of mechanical movement is a highly sensitive process, ultimately able to detect movements on the order of a wavelength of light (about 0.6 micro meters for coherent light from a Helium-Neon laser). For this reason the sensitivity of this invention in detecting small motion amplitudes is significantly higher than with prior art techniques.

FIG. 1 shows an apnea alarm and heartbeat monitor system in accordance with the current invention. A suitable coherent light source 1, advantageously a single-frequency GaAlAs injection laser diode, is driven by a continuous electrical current that is supplied by a conventional current source (not shown). Laser 1 is positioned relative to one end 21 of a multimode fiber 2 so that the light emitted by laser 1 is efficiently coupled into the fiber 2. Fiber 2 is conveniently about one to five meters in length; a suitable fiber, for example, would be a plastic fiber similar to the 250 micron core, step-index, "ESKA" plastic fiber manufactured by Mitsubishi Cable America, Inc., 520 Madison Ave,. New York, NY 10022. Fiber 2 is woven into or otherwise mechanically coupled to a mat or blanket 3 or other item of bed clothes or sleepware to provide a motion sensitive mechanical interface between the fiber 2 and the object being monitored (not shown). The output end 22 of fiber 2 emits a cone of laser light 4, all or part of which illuminates the photosensitive plane 51 of photodetector 5, conveniently a silicon PIN detector located at an appropriate distance which provides a strong modal noise current at the output 52 of detector 5. This output noise current signal is passed to the input 60 of an electronic alarm system 6. A speckle pattern of laser light will exist in the plane 51, and detector 5 will advantageously intercept approximately half the speckle cells of that pattern.

As is known to those skilled in the art, such speckle patterns are found to be composed of many randomly shaped and positioned bright spots separated by randomly shaped dark regions. When the mid section 23 of fiber 2 is moved mechanically, the speckle pattern in plane 51 changes rapidly to one that is uncorrelated to the initial pattern. This is because the speckle pattern in plane 51 is the final result of the constructive or destructive interference among the light waves guided in each of the independent "modes," or optical paths, within fiber 2 along which laser light from source 1 is guided. Moving fiber 2 changes many or all of those path lengths minutely, or causes waves guided in one mode to be coupled into another mode, with a resulting change in optical path length. Such changes of path length need average only a fraction of a wavelength of light (i.e., about 0.4 micrometer) to substantially or totally alter the resulting speckle pattern in plane 51. Fiber bending motions of a few tenths of a mm are sufficient to cause optical path shifts of this magnitude.

As is well known to those skilled in the art, the individual bright speckles are of constant or slowly changing average size which, in turn, is determined by the following factors: the numerical aperture and core diameter of fiber 2; the wavelength of the light emitted by laser 1; the distance from the fiber end 22 to the detector plane 51; and the shape of the refractive index distribution across the core of fiber 2. Typically, fiber 2 has either a "step-index distribution", in which the refractive index is constant across the core, or a "graded-index" distribution, in which the refractive index decreases approximately parabolically with radial distance from the fiber axis. For the step index case, the average speckle size is nearly constant across the speckle pattern in plane 51. On the other hand, for the gradient index fiber case, the average speckle size increases near the edge of the speckle pattern. Speckle patterns arising in fiber optic systems have been extensively studied in connection with the noise, termed "modal noise," that such effects can generate in, for example, fiber optical data links and local area computer networks. One such study is reported in "Modal noise in multimode optical fibers," by Eric G. Rawson and Joseph W.Goodman, published in Society of Photo-Optical Instrumentation Engineers (SPIE) Vol. 355, *Fiber Optics: Short-Haul and Long-Haul Measurements and Applications* (1982), pp. 37–42, and also in "Statistics of modal noise in fibers: a case of constrained speckle," by Joseph W. Goodman and Eric G. Rawson, published in Optics Letters, vol. 6, page 324, July, 1981, both of which reports are hereby incorporated by reference.

It is well known by those skilled in the science of optical speckle that the higher the coherence of the laser light source, the higher the contrast in the speckle pattern. In the scientific literature, speckle contrast C is defined by the equation $C=(I_{max}-I_{min})/(2.\times I_{mean})$, where $I_{max}$ and $I_{min}$ are the highest and lowest intensities observed locally within the speckle pattern and $I_{mean}$ is the mean intensity observed across an extended portion of the speckle pattern. As is well known to those skilled in the art, a perfectly coherent laser (that is, a laser emitting in a single longitudinal mode and a single transverse mode) results in a speckle pattern contrast equal to 1.0; and a relatively incoherent source (that is, a laser emitting in two or more longitudinal modes, or in two or more transverse modes, or a two or more each of both classes of modes) will yield a speckle pattern with a lower contrast. The lower the speckle contrast, the lower will be the model noise current associated with changes in the speckle pattern. Thus, as will be appreciated by one skilled in the art, a perfectly coherent laser source is preferred over a partially coherent laser in this invention because it will yield a higher modal noise current, and hence higher sensitivity to motion. However, a partially coherent laser source can be used in this invention with a corresponding reduction in sensitivity to motion.

While there are clearly many different ways in which the output modal noise current signal could be electronically processed to derive a suitable apnea alarm signal, a preferred embodiment is illustrated in FIG. 1. As shown, the electronic alarm system 6 is comprised typically of an amplifier and limiter 61 which amplifies the noise current and limits its amplitude, while preserving its frequency content. As is well known to those skilled in the electronics arts, the amplifier may require automatic gain control and AC coupling to accomplish this effectively. The output of amplifier/limiter 61 is passed through a band-pass or high-pass electronic filter 62 which selectively passes the high frequency components of particular relevance in apnea detection. This filtered AC signal then is applied to a rectifier circuit 63 which derives a DC output signal whose amplitude is proportional to the amplitude of the filtered AC signal. The rectified signal, in turn, is passed to an integrator 64 which integrates the rectified signal for a suitable time which is of the order of a fraction of a normal breath period (that is, this integration time constant might be about a tenth of a second). These parameters are adjusted to selectively maximize the signals attributable to fiber velocities during normal breathing. A threshold detector 65 monitors the output of the integrator 64 to signal a logic processor 66 when a normal breath event is sensed. This enables the logic processor 66 to trigger an alarm 67 if normal breathing ceases for a sustained period (which might be about 15 seconds), or if breathing occurs with abnormally high frequency for a sustained period (which might be about one minute). The latter condition would be an indication of distressed breathing which, as mentioned above, the present invention is also able to detect and report. Similarly, normal heartbeat patterns can be distinguished from abnormal patterns.

It will be understood by those versed in the art that there are many alternative ways in which the electronic subsystem of this invention can be implemented. In particular, we mention the following possibilities, which listing is not intended to be exhaustive:

1) The amplifier/limiter 61 may advantageously be implemented as an amplifier only, with the amplitude information in the noise current signal being preserved in addition to its frequency content.

2) Multiple optical detectors can be implemented, each with independent electronic sub-systems, each capable of triggering a shared or dedicated alarm based on different conditions, or each independently monitoring the same condition to provide more reliable detection of an abnormal state in the object being monitored.

3) The outputs of multiple detectors can be combined using conventional common mode rejection techniques to cancel out the common mode components of their signals, thereby discriminating against any fluctuations or drift in the optical power level emitted by the laser source.

Figure 2:
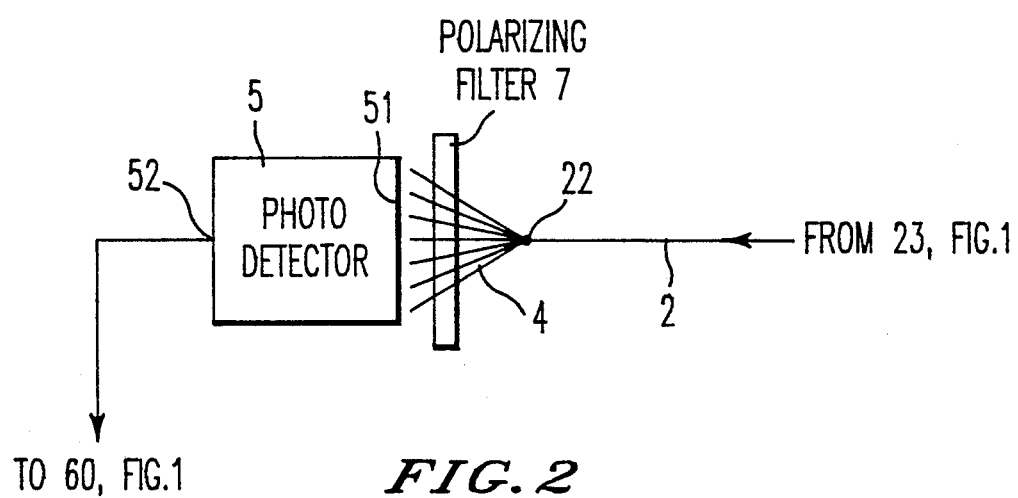
FIG. 2 is a fragmentary schematic diagram of an alternative fiber/photodetector interface for the system shown in FIG. 1.

4) A detector can be placed to accept the full cone of light emerging from the fiber, but with a polarizing filter, such as is shown at 7 in FIG. 2, placed between the output end 22 of fiber 2 and the photo detector 5. (Since each guided mode in the fiber is actually comprised of two degenerate modes with orthogonal optical polarizations, this has the effect of detecting only half the guided modes; modal noise currents will thus arise due to the exchange of guided optical power between these orthogonal polarizations. This is the case referred to earlier as the "polarizing filter case.")

5) Multiple frequency band sensing can be implemented electronically, by which means additional information about breathing dynamics can be derived.

It will be further understood by one skilled in the art that a so-called single-mode fiber (or, more precisely, a double-mode fiber when both orthogonal polarizations are taken into account), while perhaps not the preferred embodiment because of its possibly greater cost and fragility, as well as the increased alignment accuracy that is required to couple light into it, is usable in this invention. Modal noise, while sometimes not as strong in single-mode fibers, does occur due to at least two causes. Firstly, bending of a single-mode fiber causes a change in the fraction of the guided light which is coupled to non-guided (lossy) higher-order modes, contributing to a change in guided optical power as the fiber moves. Secondly, in the case of a single-mode fiber which guides both polarizations of light in a single transverse mode, part of the light guided in one polarization may be switched by fiber motion to the orthogonal polarization. Thus, in that case, a polarizer that is placed between the output end of the fiber and the optical detector, as discussed earlier as the "polarizing filter case," in position to intercept the full cone of light emerging from the fiber, will yield a strong modal noise current in the detector, since light in one polarization will not reach the detector and light in the other polarization will reach the detector nearly unattenuated. Indeed, it will be noted that the foregoing arrangement meets the criterion cited earlier for maximum noise current signal; namely, that the detector be coupled to half the guided modes. This single-mode fiber case is further advantaged in that, there being only one speckle cell, the fluctuations are of maximum possible amplitude, expressed as a percent of the total guided power, since the instantaneous power in the observed polarization mode ranges from 100% of the guided power to 0% of the guided power.

The smaller the number of modes guided by the optical fiber 2, the larger will be the RMS noise current when expressed as a fraction of the average photo current at detector 5. More particularly, the average photo current at detector 5 is essentially a constant proportional to the average total optical power guided by the fiber 2. Thus, in general, for a given laser input power, and assuming the photo detector intercepts half of the speckle cells, and neglecting input coupling losses and attenuation in the fiber 2 (both of which are typically small or negligible), the smaller the number of modes which the optical fiber 2 guides, the larger will be the RMS noise current expressed as a fraction of the total guided optical power. As is known, the number of modes which a fiber guides is proportional to the product of the fiber core diameter and the fiber numerical aperture, and is affected also by the radial distribution of the core's refractive index. It therefore follows that these fiber parameters should optimally be chosen to yield as few guided modes as possible, consistent with maintaining an appropriately broad tolerance on the precision with which the laser diode 1 and the input fiber end 21 need to be aligned for efficient and stable optical power input coupling. As noted above, this may make the choice of a single-mode fiber less practical than a multimode fiber.

An improved plastic multimode optical fiber could be specially fabricated for this application to support significantly fewer guided modes than plastic step-index fibers currently available commercially. An example of such a specially prepared fiber would be one with a significantly smaller core diameter. Plastic optical fibers which are readily available commercially typically have core diameters of 0.25 to 1.0 mm. A specially fabricated multimode plastic fiber with a core diameter of 50 μm, for example, would as explained above, yield a significantly larger RMS noise current when expressed as a fraction of the average current. For example, a 50 μm core diameter fiber would yield a 100-fold increase in RMS modal noise current compared to an otherwise identical 0.5 mm core diameter fiber, since the number of modes supported is proportional to the cross-sectional area of the core, other factors being equal. Moreover, such a custom fiber would be significantly easier to align to a laser source than a single-mode fiber, for example. As will be appreciated, a larger RMS noise current will, in turn, result in simplified, lower-cost electronics with increased freedom from electronic amplifier noise effects, and/or increased sensitivity of the invention of mechanical motion of the optical fiber. Such an increase in sensitivity could, for example, be sufficient to enable the invention to more reliably monitor heartbeat, or to permit more reliable detection of breathing behaviors when the fiber is attached to a mattress cover and positioned under and infant. It should be also noted that 50 μm core diameter fiber is readily available in glass or fused silica form. While such fibers present an increased risk of breakage in the current invention due to their greater brittleness, the use of glass or fused silica fibers may be practical in this invention provided the fibers are adequately protected by bend-resistant plastic buffer layers about the fiber. Thus, the invention is not restricted to the use of plastic fibers.

As noted above, the current invention can be used for monitoring a variety of bodily functions, as for example heartbeat and respiration during a medical treadmill test, or for monitoring irregularities in bodily function including, but not limited to, irregular or interrupted breathing, and irregular or interrupted heartbeat. This invention permits appropriate record-keeping mechanisms, notification mechanisms, or alarms to be triggered in response to abnormalities in the motion associated with these types of events.

Indeed, while the invention has been described in the context of its application to apnea detection and alarm and heartbeat monitoring, as well as the monitoring of motion producing bodily functions and for medical measurement applications such as treadmill testing, it will be evident that the invention can also be used more generally to monitor and analyze the motions of any moving object to which an optical fiber can be compliently coupled, or made to move with that object due to the motion of some intermediate agent such as a viscous fluid. Thus, all such applications are intended to be covered in the scope of this invention.

What is claimed is:

1. A fiber optic motion monitor comprising:
   a light source,
   an optical fiber waveguide including an input end, and an output end, and a sensing section intermediate said input and output ends, said optical fiber being positioned to receive light from said light source at said input end,
   movable means for transmitting motion of an object being monitored, said sensing section being coupled to said moveable means so as to move therewith,
   photodetector means positioned proximate to said output end for receiving therefrom a speckle pattern of light representative of approximately half the light guided by said optical waveguide, which pattern changes in response to movement of said sensing section, said photodetector means generating electrical signals representative of changes in said speckle pattern, and
   means for identifying electrical signals indicative of normal motion and for differentiating them from electrical signals indicative of deviations from normal motion.

2. The motion monitor as defined in claim 1 wherein the light source is a coherent laser light source.

3. The motion monitor as defined in claim 1 wherein the light source is a partially coherent laser light source.

4. The motion monitor as defined in claim 1 wherein said photo detector means is positioned to detect approximately half the light guided by said optical fiber waveguide.

5. The motion monitor as defined in claim 4 wherein said photo detector is positioned so as to be illuminated by approximately half of said speckle pattern.

6. The motion monitor as defined in claim 4 wherein a polarizing filter is interposed between said photo detector and said output end of said optical fiber waveguide so as to allow approximately half of the light guided by said optical fiber to illuminate said detector.

7. The motion monitor as defined in claim 1 further comprising alarm means triggered by said electrical signals indicative of deviations from normal motions.

8. The motion monitor as defined in claim 1 further comprising recording means for making a record of motions of the object being monitored.

9. The motion monitor as defined in claim 7 wherein said means for identifying and differentiating electrical signals is adapted to monitor at least one predetermined human bodily function, and said alarm means may be initiated in response to abnormalities in said human bodily function.

10. The motion of claim 9 wherein said human bodily function is breathing, and said alarm means is initiated in response to at least one abnormality of breathing in said human.

11. The motion monitor of claim 10 wherein said one breathing abnormality is cessation of breathing.

12. The motion monitor of claim 10 wherein said one breathing abnormality is excessively rapid breathing.

13. The motion monitor of claim 9 wherein said human bodily function is rate of heartbeat, and said alarm means is initiated in response to at least one abnormality of heartbeat in said human.

14. The motion monitor of claim 13 wherein said one heartbeat abnormality is cessation of heartbeat.

15. The motion monitor of claim 13 wherein said one heartbeat abnormality is excessively rapid heartbeat.

16. The motion monitor as defined in claim 1, wherein said means for identifying electrical signals comprises:
   bandpass filter means for filtering the electrical signals generated by said photodetector means;
   rectifier means rectifying signals filtered by said bandpass filter means;
   integrator means for integrating signals rectified by said rectifier means; and
   threshold detector means for detecting when the signals integrated by said integrator means exceed a predetermined threshold; and
   logic processor means for determining when signals produced by said threshold detector means are indicative of deviations from normal motion.

17. The motion monitor as defined in claim 9, wherein said means for identifying electrical signals comprises:
   bandpass filter means for filtering the electrical signals generated by said photodetector means;
   rectifier means for rectifying signals filtered by said bandpass filter means;
   integrator means for integrating signals rectified by said rectifier means;
   threshold detector means for detecting when the signals integrated by said integrator means exceed a predetermined threshold; and
   logic processor means for determining when signals produced by said threshold detector means are indicative of deviations from normal motion.

18. The motion monitor as defined in claim 10, wherein said means for identifying electrical signals comprises:
   bandpass filter means for filtering the electrical signals generated by said photodetector means;
   rectifier means for rectifying signals filtered by said bandpass filter means;
   integrator means for integrating signals rectified by said rectifier means;
   threshold detector means for detecting when the signals integrated by said integrator means exceed a predetermined threshold; and
   logic processor means for determining when signals produced by said threshold detector means are indicative of deviations from normal motion.

19. The motion monitor as defined in claim 11, wherein said means for identifying electrical signals comprises:
   bypass filter means filtering the electrical signals generated by said photodetector means;
   rectifier means for rectifying signals filtered by said bandpass filter means;
   integrator means for integrating signals rectified by said rectifier means;
   threshold detector means for detecting when the signals integrated by said integrator means exceed a predetermined threshold; and
   logic processor means for determining when signals produced by said threshold detector means are indicative of deviations from normal motion.

* * * * *